(12) United States Patent
Valdez et al.

(10) Patent No.: US 9,168,129 B2
(45) Date of Patent: Oct. 27, 2015

(54) ARTIFICIAL HEART VALVE WITH SCALLOPED FRAME DESIGN

(71) Applicant: Edwards Lifesciences Corporation, Irvine, CA (US)

(72) Inventors: Michael G. Valdez, Riverside, CA (US); Tram Ngoc Nguyen, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/171,221

(22) Filed: Feb. 3, 2014

(65) Prior Publication Data
US 2014/0228945 A1 Aug. 14, 2014

Related U.S. Application Data

(60) Provisional application No. 61/763,852, filed on Feb. 12, 2013.

(51) Int. Cl.
A61F 2/24 (2006.01)
(52) U.S. Cl.
CPC ............ *A61F 2/2412* (2013.01); *A61F 2/2418* (2013.01); *A61F 2220/0075* (2013.01)
(58) Field of Classification Search
CPC ..................... A61F 2/2412; A61F 2/2418
USPC ................................... 623/2.1–2.19
See application file for complete search history.

(56) References Cited

U.S. PATENT DOCUMENTS

| 3,409,013 | A | 11/1968 | Berry |
| 3,472,230 | A | 10/1969 | Fogarty et al. |
| 3,548,417 | A | 12/1970 | Kisher |
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |

(Continued)

FOREIGN PATENT DOCUMENTS

| DE | 2246526 | 3/1973 |
| DE | 19532846 | 3/1997 |

(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

(Continued)

*Primary Examiner* — Jason-Dennis Stewart
(74) *Attorney, Agent, or Firm* — Klarquist Sparkman, LLP; David L. Hauser

(57) ABSTRACT

Implantable prosthetic valves are disclosed, methods of their use, and related fabrication techniques are disclosed. In some cases, the prosthetic valves disclosed herein can include frame, skirt, and valve components. The frame component can have an overall, generally scalloped shape comprising fewer struts and fabricated from less raw material than known frames. In some cases, the prosthetic valves disclosed herein can be crimped to a smaller diameter than can other known valves.

19 Claims, 8 Drawing Sheets

(56) References Cited

U.S. PATENT DOCUMENTS

| | | |
|---|---|---|
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,141,494 A | 8/1992 | Danforth et al. |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A | 7/1999 | Khosravi |
| 5,957,949 A | 9/1999 | Leonhardt et al. |
| 5,968,068 A | 10/1999 | Dehdashtian |
| 5,980,570 A | 11/1999 | Simpson |
| 5,984,959 A | 11/1999 | Robertson |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen |
| 6,245,102 B1 | 6/2001 | Jayaraman |
| 6,299,637 B1 | 10/2001 | Shaolian |
| 6,302,906 B1 | 10/2001 | Goecoechea et al. |
| 6,350,277 B1 | 2/2002 | Kocur |
| 6,379,372 B1 | 4/2002 | Dehdashtian et al. |
| 6,419,695 B1 | 7/2002 | Gabbay |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely et al. |
| 6,582,462 B1 | 6/2003 | Andersen et al. |
| 6,605,112 B1 | 8/2003 | Moll |
| 6,652,578 B2 | 11/2003 | Bailey et al. |
| 6,730,118 B2 | 5/2004 | Spenser et al. |
| 6,733,525 B2 | 5/2004 | Pease et al. |
| 6,767,362 B2 | 7/2004 | Schreck |
| 6,830,584 B1 | 12/2004 | Seguin |
| 6,869,444 B2 | 3/2005 | Gabbay |
| 6,878,162 B2 | 4/2005 | Bales et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,160,322 B2 | 1/2007 | Gabbay |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann |
| 7,785,366 B2 | 8/2010 | Maurer |
| 7,993,394 B2 | 8/2011 | Hariton et al. |
| 8,007,992 B2 | 8/2011 | Tian et al. |
| 8,029,556 B2 | 10/2011 | Rowe |
| 8,167,932 B2 | 5/2012 | Bourang |
| 8,348,963 B2 | 1/2013 | Wilson |
| 8,407,380 B2 | 3/2013 | Matsunaga |
| 8,449,606 B2 | 5/2013 | Eliasen |
| 2001/0021872 A1 | 9/2001 | Bailey et al. |
| 2002/0032481 A1 | 3/2002 | Gabbay |

(56) References Cited

U.S. PATENT DOCUMENTS

| | | |
|---|---|---|
| 2002/0173842 A1 | 11/2002 | Buchanan |
| 2003/0036795 A1* | 2/2003 | Andersen et al. ............ 623/2.11 |
| 2003/0050694 A1 | 3/2003 | Yang et al. |
| 2003/0100939 A1 | 5/2003 | Yodfat et al. |
| 2003/0158597 A1 | 8/2003 | Quiachon |
| 2003/0212454 A1 | 11/2003 | Scott et al. |
| 2004/0039436 A1 | 2/2004 | Spenser et al. |
| 2004/0133263 A1 | 7/2004 | Dusbabek et al. |
| 2004/0186563 A1 | 9/2004 | Iobbi |
| 2004/0186565 A1 | 9/2004 | Schreck |
| 2004/0260389 A1 | 12/2004 | Case et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0229719 A1 | 10/2006 | Marquez et al. |
| 2006/0259135 A1 | 11/2006 | Navia et al. |
| 2006/0259137 A1 | 11/2006 | Artof et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0027534 A1 | 2/2007 | Bergheim et al. |
| 2007/0088431 A1 | 4/2007 | Bourang et al. |
| 2007/0112422 A1 | 5/2007 | Dehdashtian |
| 2007/0203503 A1 | 8/2007 | Salahieh et al. |
| 2007/0203575 A1 | 8/2007 | Forster et al. |
| 2007/0265700 A1 | 11/2007 | Eliasen |
| 2007/0270943 A1 | 11/2007 | Solem |
| 2008/0004688 A1* | 1/2008 | Spenser et al. ............... 623/1.13 |
| 2008/0065011 A1 | 3/2008 | Marchand et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2009/0157175 A1 | 6/2009 | Benichou |
| 2009/0164005 A1 | 6/2009 | Dove et al. |
| 2009/0171456 A1 | 7/2009 | Kveen et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0049313 A1 | 2/2010 | Alon et al. |
| 2010/0198347 A1 | 8/2010 | Zakay |
| 2010/0204781 A1 | 8/2010 | Alkhatib |
| 2010/0262233 A1 | 10/2010 | He |
| 2011/0015729 A1 | 1/2011 | Jimenez et al. |
| 2011/0098802 A1 | 4/2011 | Braido et al. |
| 2012/0123529 A1 | 5/2012 | Levi et al. |
| 2013/0023985 A1 | 1/2013 | Khairkhahan |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1570809 | 9/2005 |
| EP | 1796597 | 6/2007 |
| FR | 2815844 | 5/2002 |
| FR | 2788217 | 7/2007 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/01768 | 2/1993 |
| WO | WO 96/40008 | 12/1996 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | WO 01/28459 | 4/2001 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2005/034812 | 4/2005 |
| WO | WO 2005/087140 | 9/2005 |
| WO | WO 2005/102015 | 11/2005 |
| WO | WO 2006/014233 | 2/2006 |
| WO | WO 2006/034008 | 3/2006 |
| WO | WO 2006/108090 | 10/2006 |
| WO | WO 2006/111391 | 10/2006 |
| WO | WO 2006/138173 | 12/2006 |
| WO | WO 2008/005405 | 1/2008 |
| WO | WO 2008/035337 | 3/2008 |
| WO | WO 2008/091515 | 7/2008 |
| WO | WO 2008/147964 | 12/2008 |
| WO | WO 2008/150529 | 12/2008 |
| WO | WO 2009/033469 | 3/2009 |
| WO | WO 2009/116041 | 9/2009 |
| WO | WO 2010/121076 | 10/2010 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl.J. Med., 1994; 331:1729-34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytinnes.com/1991/01/03/health/device-that-opens-clogged-arteries-gets-a-faili . . . , Jul. 29, 2009, 2 pages.

(56) References Cited

OTHER PUBLICATIONS

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluβ des Ductus Arteriosus Persistens ohne Thorakotomie," Thoraxchirurgie Vaskulare Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Intery Radial 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, $2^{nd}$ Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Médecine et Hygiène, Genève, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Wheatley, M.D., David J., "Valve Prostheses," Rob & Smith's Operative Surgery, Fourth Edition, pp. 416-424, Butterworths 1986.

\* cited by examiner

ARTIFICIAL HEART VALVE WITH SCALLOPED FRAME DESIGN

CROSS REFERENCE TO RELATED APPLICATION

This application claims the benefit of U.S. Patent Application No. 61/763,852, filed Feb. 12, 2013, which is hereby incorporated by reference.

FIELD

The present disclosure relates to implantable devices, and more particularly, to prosthetic valves for implantation into body ducts such as native heart valve annuluses.

BACKGROUND

The human heart can suffer from various valvular diseases, which can result in significant malfunctioning of the heart and ultimately require replacement of the native heart valve with an artificial valve. There are a number of known artificial valves and a number of known methods of implanting these artificial valves in humans.

One method of implanting an artificial heart valve in a human patient is via open-chest surgery, during which the patient's heart is stopped and the patient is placed on cardiopulmonary bypass (a so-called "heart-lung machine"). In one common surgical procedure, the diseased native valve leaflets are excised and a prosthetic valve is sutured to the surrounding tissue at the native valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from aortic stenosis who are older than 80 years cannot be operated on for aortic valve replacement.

Because of the drawbacks associated with conventional open-chest surgery, percutaneous and minimally-invasive surgical approaches are in some cases preferred. In one such technique, a prosthetic valve is configured to be implanted in a much less invasive procedure by way of catheterization. For instance, U.S. Pat. Nos. 7,393,360, 7,510,575, and 7,993,394, which are hereby incorporated herein by reference, describe collapsible transcatheter prosthetic heart valves that can be percutaneously introduced in a compressed state on a catheter and expanded to a functional size at the desired position by balloon inflation or by utilization of a self-expanding frame or stent.

An important design parameter of a transcatheter prosthetic heart valve is the diameter of the folded or crimped profile. The diameter of the crimped profile is important because it directly influences the physician's ability to advance the prosthetic valve through a femoral artery or vein. More particularly, a smaller profile allows for treatment of a wider population of patients, with enhanced safety.

SUMMARY

The present disclosure is directed toward new and non-obvious implantable prosthetic devices. In some cases, an implantable prosthetic valve comprises an inflow end, an outflow end, a central longitudinal axis extending from the inflow end to the outflow end, a radially collapsible and expandable annular frame comprising a plurality of commissure attachment posts and a plurality of sets of struts, and a valve member supported within an interior of the radially collapsible and expandable annular frame. In some cases, the plurality of commissure attachment posts are angularly spaced apart from each other around the central longitudinal axis, each set of struts extends circumferentially partially around the central longitudinal axis from a first respective commissure attachment post to a second respective commissure attachment post and comprises a plurality of rows of angled struts arranged in a zig-zag pattern in each row of angled struts, and each set of struts comprises at least one complete row of angled struts extending from the first respective commissure attachment post to the second respective commissure attachment post and at least two partial rows of angled struts extending between the first and second respective commissure attachment posts.

In some cases, each set of struts comprises exactly one complete row of angled struts extending circumferentially around the central longitudinal axis from the first respective commissure attachment post to the second respective commissure attachment post. In some cases, each set of struts comprises exactly two partial rows of angled struts extending between the first and second respective commissure attachment posts. In some cases, the two partial rows of angled struts are positioned on opposite sides of the complete row of angled struts.

In some cases, each set of struts further comprises a plurality of vertical struts extending between and connecting a first partial row of angled struts to the at least one complete row of angled struts. In some cases, a set of struts further comprises at least one additional strut extending between and connecting an end of the first partial row of angled struts and an apex of the at least one complete row of angled struts. In some cases, a second partial row of angled struts is coupled to apices of the at least one complete row of angled struts. In some cases, a set of struts further comprises at least one additional strut extending between and connecting an apex of the second partial row of angled struts and a commissure attachment post.

In some cases, each set of struts comprises an upper perimeter and a lower perimeter, each of the upper and lower perimeters having an overall concave shape facing in a direction of the outflow end of the implantable prosthetic valve. In some cases, the radially collapsible and expandable annular frame is configured to be self-expandable from a radially collapsed state. In some cases, the radially collapsible and expandable annular frame has an outer diameter of about 19 French in the radially collapsed state.

In some cases, a valve further comprises a skirt secured to the radially collapsible and expandable annular frame. In some cases, the skirt is secured to the radially collapsible and expandable annular frame with sutures securing the skirt to the plurality of sets of struts. In some cases, the skirt is secured to the radially collapsible and expandable annular frame with sutures securing the skirt to the radially collapsible and expandable annular frame through openings in the commissure attachment posts. In some cases, each set of struts comprises no more than 19 struts, 16 nodes, and 4 open cells. In some cases, a frame comprises exactly three commissure attachment posts and exactly three sets of struts.

In some cases, an implantable prosthetic valve comprises, an inflow end, an outflow end, a central longitudinal axis extending in an axial direction from the inflow end to the outflow end, a radially collapsible and expandable annular frame comprising a plurality of commissure attachment posts and a plurality of sets of struts, and a valve member supported within an interior of the radially collapsible and expandable annular frame. In some cases, the plurality of commissure attachment posts are angularly spaced apart from each other around, and are aligned with, the central longitudinal axis, each set of struts extends circumferentially partially around the central longitudinal axis from a first respective commissure attachment post to a second respective commissure attachment post, and each set of struts comprises no more than two rows of struts along any axis aligned with the central longitudinal axis.

In some cases, each set of struts comprises exactly one complete row of angled struts extending circumferentially around the central longitudinal axis from the first respective commissure attachment post to the second respective commissure attachment post. In some cases, each set of struts comprises exactly two partial rows of angled struts extending between the first and second respective commissure attachment posts. In some cases, the two partial rows of angled struts are positioned axially on opposite sides of the complete row of angled struts.

In some cases, an implantable prosthetic valve comprises an inflow end, an outflow end, a central longitudinal axis extending from the inflow end to the outflow end, a radially collapsible and expandable annular frame comprising a plurality of commissure attachment posts and a plurality of sets of struts, and a valve member supported within an interior of the radially collapsible and expandable annular frame. In some cases, the plurality of commissure attachment posts are angularly spaced apart from each other around the central longitudinal axis, and each set of struts extends circumferentially partially around the central longitudinal axis from a first respective commissure attachment post to a second respective commissure attachment post and comprises a plurality of rows of angled struts arranged in a zig-zag pattern in each row of angled struts, wherein each set of struts comprises exactly two complete rows of angled struts extending from the first respective commissure attachment post to the second respective commissure attachment post and exactly two partial rows of angled struts extending between the first and second respective commissure attachment posts.

In some cases, respective upper peripheries of each of the sets of struts comprise an uppermost node which is located closer to the inflow end of the valve than an uppermost portion of the attachment posts. In some cases, the respective upper peripheries of the sets of struts include a top apex which is located closer to the inflow end of the valve than the uppermost node. In some cases, the partial rows of angled struts are positioned on opposite sides of the complete rows of angled struts. In some cases, each set of struts further comprises a plurality of vertical struts extending between and connecting a first complete row of angled struts to a second complete row of angled struts. In some cases, a first partial row of angled struts is coupled to apices of a first complete row of angled struts and a second partial row of angled struts is coupled to apices of a second complete row of angled struts.

In some cases, each set of struts comprises an upper perimeter and a lower perimeter, each of the upper and lower perimeters having an overall concave shape facing in a direction of the outflow end of the implantable prosthetic valve. In some cases, a valve further comprises a skirt secured to the radially collapsible and expandable annular frame. In some cases, the skirt is secured to the radially collapsible and expandable annular frame with sutures securing the skirt to the plurality of sets of struts. In some cases, the skirt is secured to the radially collapsible and expandable annular frame with sutures securing the skirt to the radially collapsible and expandable annular frame through openings in the commissure attachment posts.

In some cases, an implantable prosthetic valve comprises an inflow end, an outflow end, a central longitudinal axis extending from the inflow end to the outflow end, a radially collapsible and expandable annular frame comprising a plurality of commissure attachment posts and a plurality of sets of struts, and a valve member supported within an interior of the radially collapsible and expandable annular frame. In some cases, the plurality of commissure attachment posts are angularly spaced apart from each other around the central longitudinal axis, and each set of struts extends circumferentially partially around the central longitudinal axis from a first respective commissure attachment post to a second respective commissure attachment post and comprises no more than 19 struts, no more than 20 nodes, and no more than 4 open cells.

In some cases, each set of struts comprises a first partial row of struts, a second partial row of struts, and a third partial row of struts extending circumferentially around the central longitudinal axis from the first respective commissure attachment post to the second respective commissure attachment post, and the second and third partial rows of angled struts are positioned on opposite sides of the first row of angled struts. In some cases, each set of struts further comprises a plurality of vertical struts extending between and connecting the first partial row of angled struts to the second partial row of angled struts. In some cases, a set of struts further comprises a fourth partial row of angled struts axially offset from the first partial row of angled struts toward the second partial row of struts by a distance which is half a length of the vertical struts. In some cases, the fourth partial row of angled struts forms a zig-zag arrangement which is inverted from the zig-zag arrangement of struts in the first partial row.

In some cases, an implantable prosthetic valve comprises an inflow end, an outflow end, a central longitudinal axis extending in an axial direction from the inflow end to the outflow end, a radially collapsible and expandable annular frame comprising a plurality of commissure attachment posts and a plurality of sets of struts, and a valve member supported within an interior of the radially collapsible and expandable annular frame. In some cases, the plurality of commissure attachment posts are angularly spaced apart from each other around, and are aligned with, the central longitudinal axis, each set of struts extends circumferentially partially around the central longitudinal axis from a first respective commissure attachment post to a second respective commissure attachment post, and each set of struts comprises no more than two rows of struts along any axis aligned with the central longitudinal axis. In some cases, each set of struts comprises exactly two rows of struts along any axis aligned with the central longitudinal axis and passing through the set of struts.

The foregoing and other objects, features, and advantages of the invention will become more apparent from the following detailed description, which proceeds with reference to the accompanying figures.

DETAILED DESCRIPTION

Figure 1:
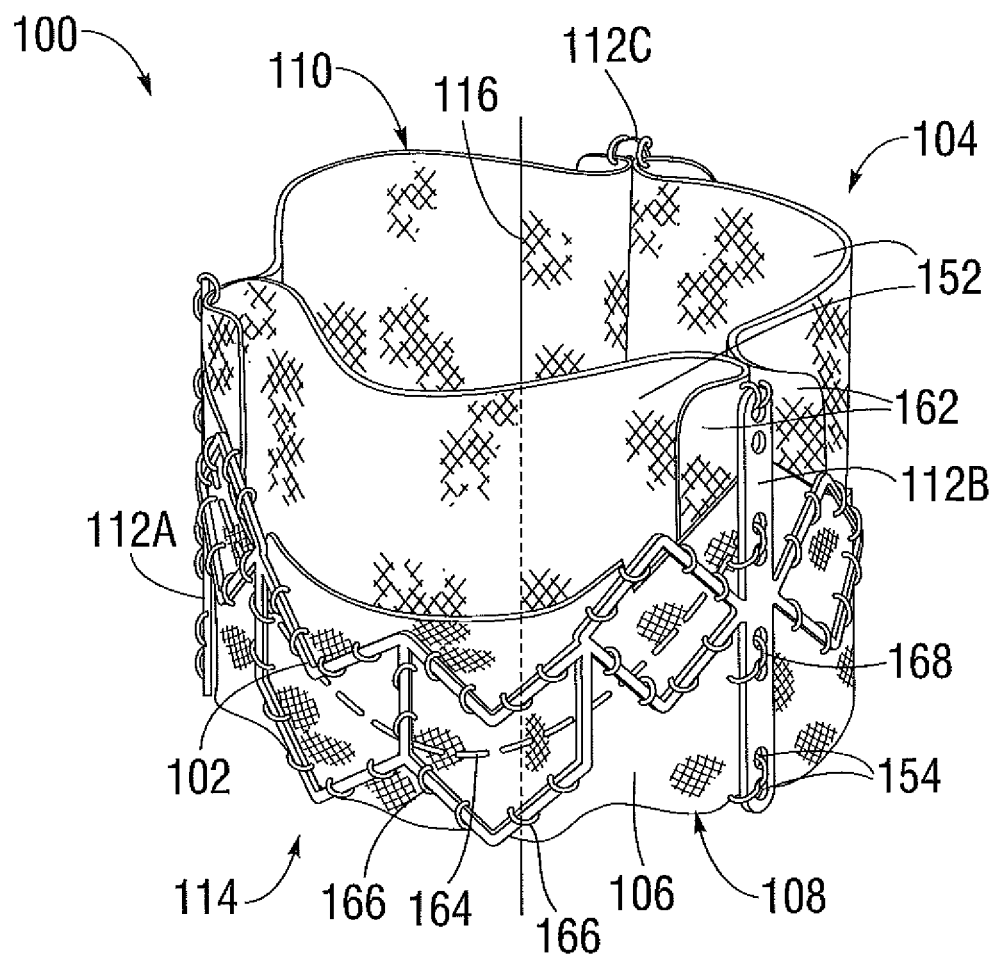
FIG. 1 is a perspective view of a representative embodiment of a prosthetic heart valve.
Figure 2:
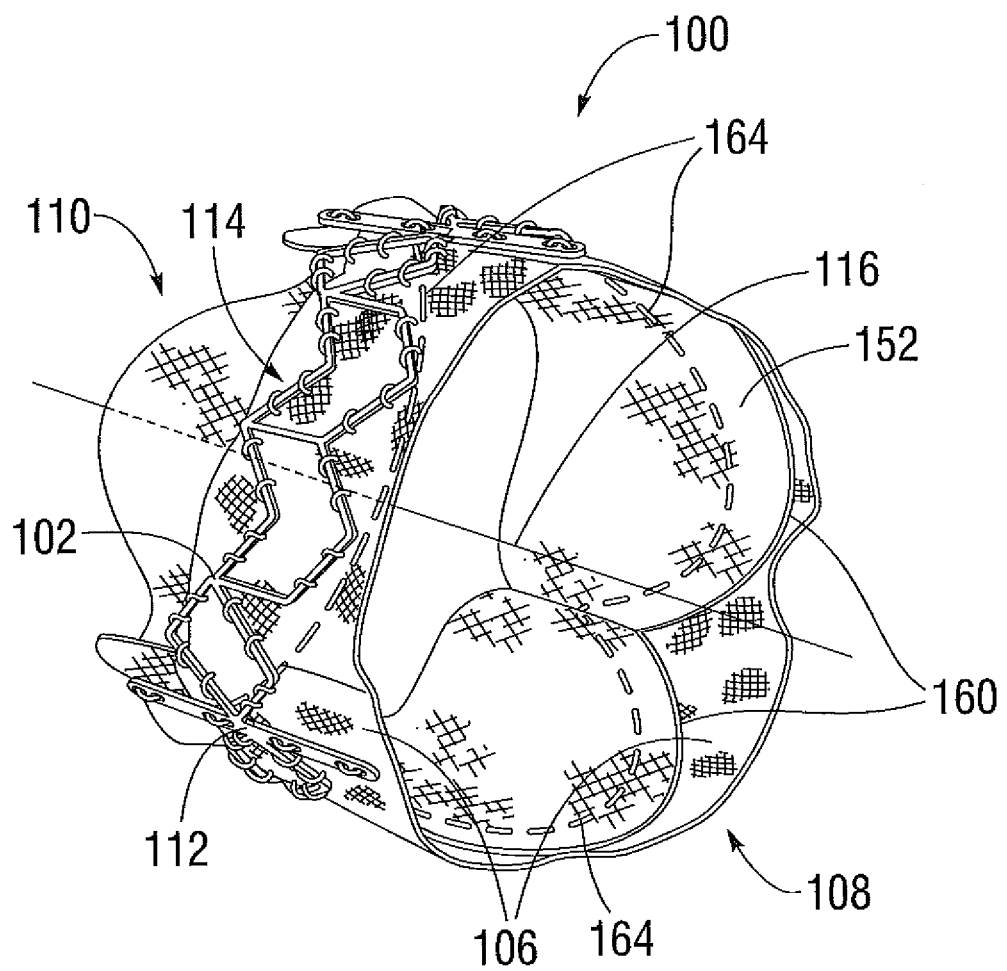
FIG. 2 is another perspective view of the prosthetic valve of FIG. 1.

FIGS. 1 and 2 illustrate an implantable prosthetic valve 100, according to one embodiment. The prosthetic valve 100 in the illustrated embodiment generally comprises a frame, or stent, 102, a skirt 106 positioned within, secured to, and supported by the frame 102, and a leaflet structure 104 positioned within, secured to, and supported by the skirt 106 and the frame 102. The prosthetic valve 100 typically is implanted in the annulus of the native aortic valve but also can be adapted to be implanted in other native valves of the heart (i.e., the mitral, pulmonary, and tricuspid) or in various other ducts or orifices of the body. The prosthetic valve 100 can be delivered to a patient's heart in a transfemoral procedure in which the prosthetic valve 100 is inserted into a femoral artery and advanced through the aorta to a native valve of a patient's heart. The prosthetic valve 100 can also be delivered in a transapical procedure in which the prosthetic valve 100 is inserted through a small surgical opening in the chest and another surgical opening in the apex of the heart. The prosthetic valve 100 can also be delivered in a transaortic procedure in which the prosthetic valve 100 is inserted through a small surgical opening in the chest and another surgical opening in the ascending aorta at a location above the native aortic valve.

When implanted, the frame 102 allows the prosthetic valve 100 to retain its overall structure, and the leaflet structure 104 allows the prosthetic valve 100 to function as a replacement for a native valve, allowing fluid to flow in one direction through the prosthetic valve 100, but not the other direction. The prosthetic valve 100 (and thus the frame 102 which is a component thereof) has a "lower" end 108 and an "upper" end 110. In the context of the present application, the terms "lower" and "upper" are used interchangeably with the terms "inflow" and "outflow," respectively. Thus, for example, when implanted in the aortic valve, the lower end 108 of the prosthetic valve 100 is its inflow end and the upper end 110 of the prosthetic valve 100 is its outflow end.

The prosthetic valve 100 and the frame 102 are configured to be radially collapsible to a collapsed or crimped state for introduction into the body on a delivery catheter and radially expandable to an expanded state for implanting the prosthetic valve 100 at a desired location in the body (e.g., the native aortic valve). The frame 102 can be made of a plastically-expandable material that permits crimping of the prosthetic valve 100 to a smaller profile for delivery and expansion of the prosthetic valve 100 using an expansion device such as the balloon of a balloon catheter. Suitable plastically-expandable materials that can be used to form the frame 102 include, without limitation, stainless steel, cobalt chromium, a nickel based alloy (e.g., a nickel-cobalt-chromium alloy), polymers, or combinations thereof. In particular embodiments, the frame 102 is made of a nickel-cobalt-chromium-molybdenum alloy, such as MP35N® alloy (SPS Technologies), which is equivalent to UNS R30035 (covered by ASTM F562-02). MP35N® alloy/UNS R30035 comprises 35% nickel, 35% cobalt, 20% chromium, and 10% molybdenum, by weight. It has been found that the use of MP35N® alloy to form a frame provides superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frame 102 can be reduced, thereby providing a lower profile prosthetic valve assembly for percutaneous delivery to the treatment location in the body.

Alternatively, the prosthetic valve 100 can be a so-called self-expanding prosthetic valve 100 wherein the frame 102 is made of a self-expanding material such as Nitinol. A self-expanding prosthetic valve 100 can be crimped to a smaller profile and held in the crimped state with a restraining device such as a sheath covering the prosthetic valve. When the prosthetic valve 100 is positioned at or near the target site, the restraining device is removed to allow the prosthetic valve to self-expand to its expanded, functional size.

As shown in FIGS. 1-2, the skirt 106 can have an upper periphery or edge which has a generally undulating or scalloped shape and which generally follows an upper boundary of sets of struts 114 of the frame 102, and a lower periphery or edge having a shape which is generally defined by a circle. In alternative embodiments, however, the upper periphery of the skirt 106 can be generally circular or any other appropriate shape, and the lower periphery can have an undulating or other appropriate shape. The skirt 106 can be formed of a tough, tear resistant material. The skirt 106 can be formed, for example, of polyethylene terephthalate (PET), or of one of various other synthetic or natural materials. The thickness of the skirt can vary, but a thinner skirt can provide for better crimping performance while still providing perivalvular sealing.

Similarly, a more stretchable and/or compressible material such as silicon can allow for a smaller crimping profile of the prosthetic valve 100. Other materials that can be used to form the skirt 106 include, but are not limited to, PTFE, ePTFE, polyurethane, polyolefins, hydrogels, biological materials (e.g., pericardium or biological polymers such as collagen, gelatin, or hyaluronic acid derivatives) or combinations thereof. The skirt 106 can be made of an auxetic and/or swelling material, such as synthetic or natural hydrogels. Skirt 106 can serve several functions, including, for example, sealing and decreasing perivalvular leakage, anchoring the leaflet structure 104 to the frame 102, and protecting leaflets 152 from damage caused by being pinched during crimping or working cycles of the prosthetic valve 100 itself. Further details regarding the skirt 106 are available in U.S. Pat. No. 7,993,394, which is incorporated by reference.

The leaflet structure 104 can comprise three leaflets 152 which can be arranged to collapse in a tricuspid arrangement, as best shown in FIGS. 1-2. As shown in FIGS. 1-2, each leaflet 152 can be positioned such that a first end of the leaflet 152 is attached to a first attachment post 112, and a second end of the leaflet 152 is attached to an adjacent attachment post 112. As shown in FIG. 2, a lower edge 160 of the leaflet structure 104 desirably has an undulating, curved, scalloped shape. By forming the leaflets 152 with this scalloped geometry, stresses on the leaflets 152 can be reduced, which in turn can improve durability of the prosthetic valve 100. Moreover, by virtue of the scalloped shape, folds and ripples at the central region of each leaflet, which can cause early calcification in those areas, can be reduced or eliminated. The scalloped geometry can also reduce the amount of tissue material used to form the leaflet structure 104, thereby allowing a smaller, more even crimped profile at the inflow end 108 of the prosthetic valve 100. The leaflets 152 can be formed of pericardial tissue (e.g., bovine pericardial tissue), biocompatible synthetic materials, or various other suitable natural or synthetic materials as known in the art and described in U.S. Pat. No. 6,730,118, which is hereby incorporated herein by reference. Further details regarding the leaflet structure 104 are available in U.S. Pat. No. 7,993,394, which is incorporated by reference.

The leaflet structure 104 can be attached to the skirt 106 and/or the frame 102, and the skirt 106 can be secured to the inside of the frame 102, thereby coupling the leaflet structure 104 to the frame 102. In one particular exemplary embodiment, the lower edge 160 of each leaflet 152 can be stitched to the skirt 106. As shown in FIGS. 1 and 2, the leaflets 152 can be stitched to the skirt 106 by stitching 164. The skirt 106 can be sutured to individual struts with sutures 166 and to openings 154 in the attachment posts 112 with sutures 168. Each leaflet 152 can have opposing side portions 162 (also referred to as tab portions), each of which can be sutured to an adjacent side portion 162 of another leaflet 152, thereby forming commissures of the leaflet structure 104. Each commissure can be aligned with a respective attachment post 112. Each commissure can be secured to an attachment post with sutures 168 extending through the side portions 162 and the openings 154 in the attachment post 112.

As another particular example, the frame 102 can be dipped into liquid silicone to form a skirt of silicone, which can cover the entire frame and in some cases span the openings of open cells in the frame 102. Further details regarding the methods of securing the various components of the prosthetic valve 100, including the frame 102, the leaflet structure 104, and the skirt 106 to one another are available in U.S. Pat. No. 7,993,394, which is incorporated by reference.

Figure 3:
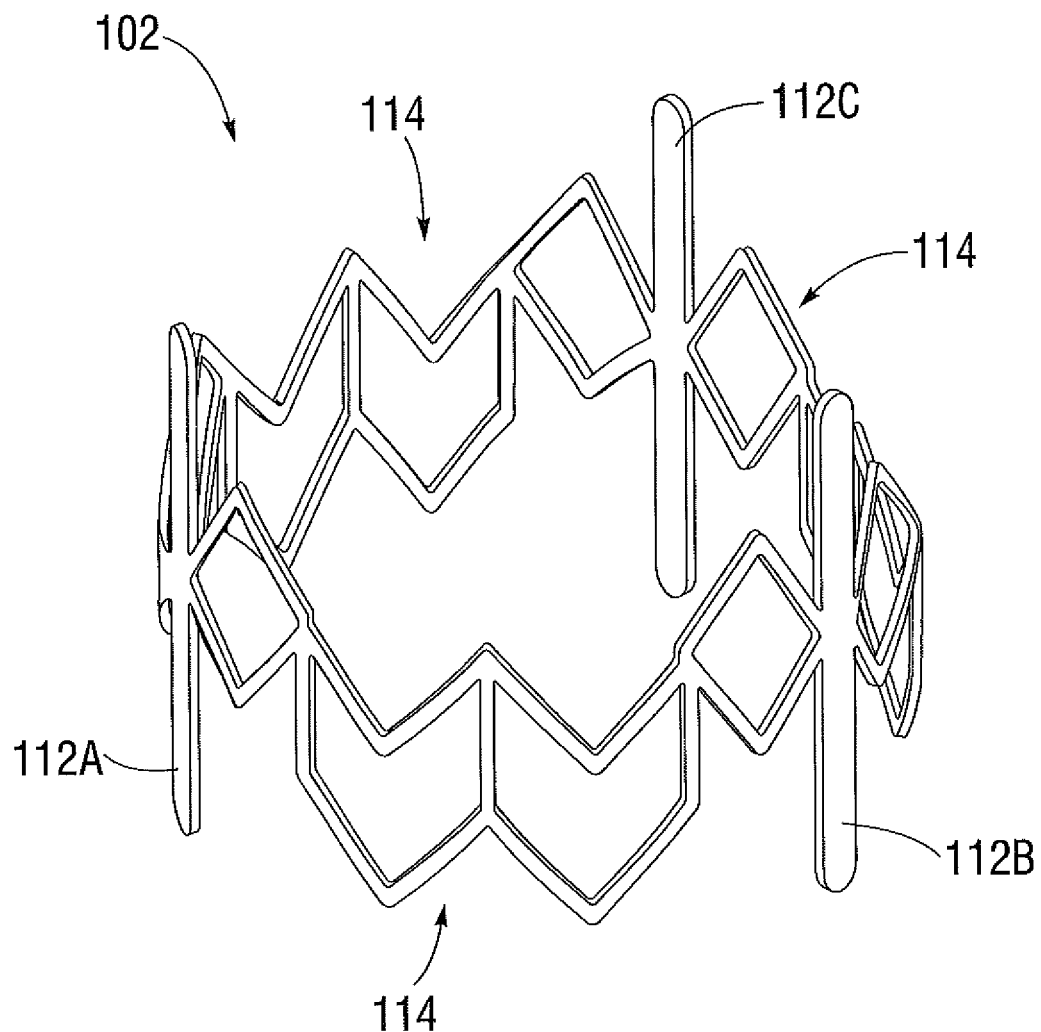
FIG. 3 is a perspective view of the frame of the prosthetic valve of FIG. 1.

FIG. 3 shows the frame 102 alone for purposes of illustration. Referring to FIGS. 1-3, the frame 102 can be an annular, stent-like structure having a plurality of angularly spaced, vertically extending, commissure attachment posts, or struts 112. The attachment posts 112 can extend substantially the entire distance from the lower end 108 to the upper end 110 of the prosthetic valve 100, and, as illustrated in FIGS. 1-2, can include several openings 154, to which other components of the prosthetic valve 100 can be attached (e.g., stitched). As shown in FIGS. 1-3, the frame 102 can comprise three attachment posts 112A, 112B, and 112C, angularly spaced apart from each other by approximately one hundred and twenty degrees. Each of the posts 112A, 112B, 112C can be coupled to each of the adjacent posts by a set of struts 114. Together, the three sets of struts 114 and the attachment posts 112 form the annular structure of the frame 102. The frame 102 can have a central longitudinal axis 116 which extends axially through the center of the annular structure of the frame 102 in a direction parallel to the attachment posts 112A, 112B, 112C. Thus, each set of struts 114 comprises an interconnected web of individual struts which curves approximately one hundred and twenty degrees around the axis 116.

Figure 4A:
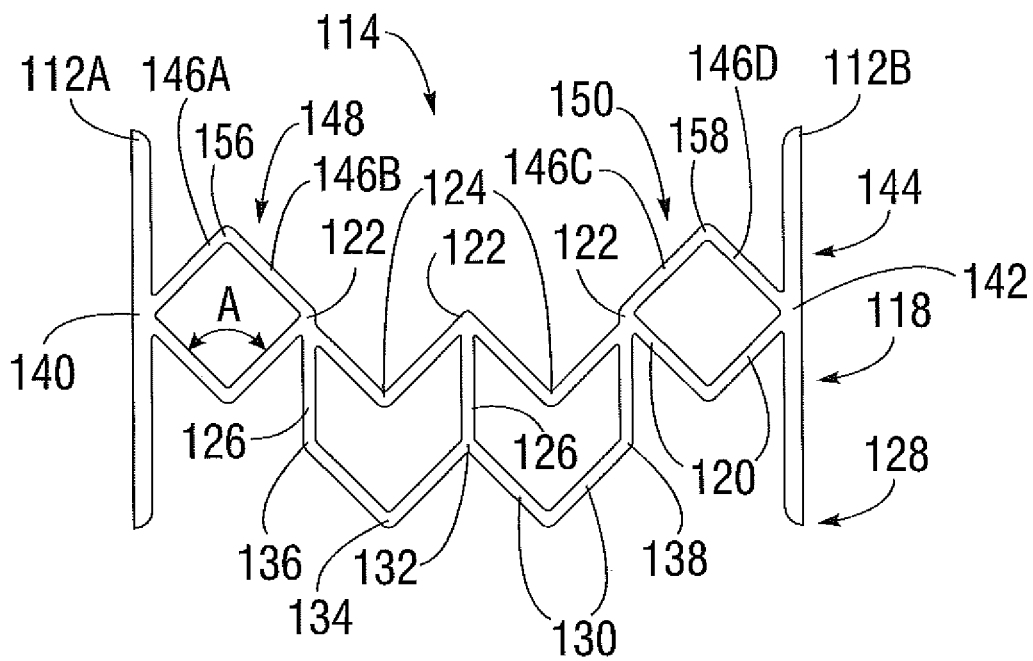
FIGS. 4A-B are flattened views of a 120-degree segment of the frame shown in FIG. 3.
Figure 4B:
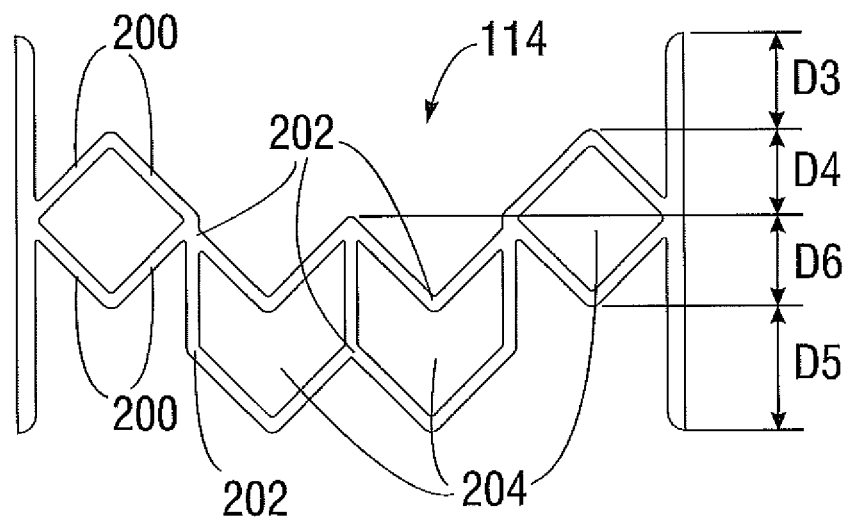

FIGS. 4A-B each show an identical flattened view of a segment of the frame 102 extending between the attachment posts 112A and 112B. The segment shown includes half of attachment post 112A, half of attachment post 112B, and a set of struts 114. As shown in FIG. 4A, each set of struts 114 can comprise a main row 118 comprising eight individual struts 120. The struts 120 can be arranged in a generally zig-zag or saw-tooth pattern extending circumferentially partially around the axis 116. The main row 118 can have a first end 140 connected to a first attachment post 112A and a second end 142 connected to a second attachment post 112B. The main row of struts 118 is a complete row of angled struts. As used herein, a "complete" row of angled struts is a series of struts connected end to end from a first attachment post to a second attachment post and arranged in a zig-zag or saw-tooth configuration in which each connection of adjacent struts forms either a top apex or a bottom apex. A "partial" row of struts is one that is not complete.

The struts 120 of the main row 118 can be further arranged so that the zig-zag pattern includes three top apices 122 pointing toward the upper end 110 of the frame 102 and four bottom apices 124 pointing toward the lower end 108 of the frame 102. A vertical strut 126 can be attached to a top apex 122 and extend away from the top apex 122 toward the lower end 108 of the frame 102. In the embodiment illustrated in FIGS. 1-4, a respective vertical strut 126 is provided for each top apex 122, and each of the vertical struts 126 extend from the respective top apex 122 toward the lower end 108 of the frame 102.

Each set of struts 114 can further comprise a secondary row 128 adjacent the inflow end 108 of the frame 102 comprising four individual struts 130. The struts 130 can be arranged in a generally zig-zag or saw-tooth pattern extending circumferentially partially around the axis 116. Thus, each strut 130 can be parallel to and displaced from one of the struts 120 in the main row. The struts 130 can be further arranged so that the zig-zag pattern includes one secondary top apex 132 pointing toward the upper end 110 of the frame 102 and two secondary bottom apices 134 pointing toward the lower end 108 of the frame 102. The secondary row 128 has first and second ends 136, 138, respectively, that desirably are spaced from and not connected to the commissure attachment posts 112A, 112B. The first end 136, second end 138, and secondary top apex 132 can be connected to respective vertical struts 126, thus, as illustrated in FIG. 4A, the secondary row 128 can be coupled to the main row 118 via the three vertical struts 126.

Each set of struts 114 can further comprise a tertiary row 144 comprising a first pair 148 and a second pair 150 of angled struts. The first pair of struts 148 can comprise angled struts 146A and 146B, and the second pair of struts 150 can comprise angled struts 146C and 146D. The strut 146A can be connected at one end to the attachment post 112A and the first end 140 of the main row 118, and at its other end to an adjacent end of the strut 146B to form a top apex 156. The strut 146B can be connected at one end to the top apex 156 and at its other end to a respective top apex 122 of the main row.

The second pair of struts 150 can have an arrangement similar to that of the first pair 148. Thus, the strut 146D can be connected at one end to the attachment post 112B and the second end 142 of the main row 118, and at its other end to an adjacent end of the strut 146C to form a top apex 158. The strut 146C can be connected at one end to the top apex 158 and at its other end to a respective top apex 122 of the main row. As shown in FIG. 4A, the tertiary row 144 desirably does not include any struts within the space defined between the struts 146B and 146C.

Adjacent struts in one of the main, secondary, and/or tertiary rows can be connected to one another to form an angle A. The selection of angle A can affect the strength of the frame 102 when expanded and can affect the ease with which the frame 102 can be crimped and/or expanded in the manner described below. In some embodiments, the angle A is between ninety and one hundred and ten degrees, with about one hundred degrees being a specific example.

In accordance with the foregoing description, a set of struts 114 can be described as comprising a plurality of individual struts 200 connected at a series of nodes (a node includes either the location of a connection between two struts or the location of a connection between a strut and an attachment post) 202, thereby defining a cellular structure having a plurality of open cells (including cells formed partially by an attachment post) 204. As shown in FIG. 4B, a set of struts 114 in the illustrated embodiment can include not more than 19 individual struts 200, 16 nodes 202, and 4 open cells 204. The frame 102 can comprise three sets of struts 114, each having substantially the same structure, each extending between and connecting two of the attachment posts 112A, 112B, 112C, and each curving approximately one hundred and twenty degrees around the axis 116.

As also shown in FIGS. 4A and 4B, an upper periphery of the set of struts 114 can include top apices 156, 158, and 122. An uppermost node of the set of struts 114 (e.g., one of top apices 156, 158) can be located below an uppermost portion of the attachment posts 112A, 112B. More specifically, an uppermost node of the set of struts 114 can be positioned towards the lower end of the frame relative to an uppermost portion of the attachment posts by a distance D3. Further, the upper periphery of the set of struts 114 can include a top apex of the main row (e.g., one of top apices 122) that is located below the uppermost node of the set of struts 114. More specifically, the upper periphery of the set of struts 114 can include a top apex 122 that is located closer to the lower end of the frame than the uppermost node 156 and/or 158 of the set of struts 114 by a distance D4.

Similarly, a lower periphery of the set of struts 114 can include a bottom apex of the main row (e.g., one of bottom apices 124) that is located above a lowermost portion of the attachment posts 112A, 112B, such as by a distance D5. FIG. 4B also shows that the upper periphery of the set of struts 114 can extend below a location where the set of struts 114 is connected to the attachment posts (e.g., at first or second ends 140 or 142), e.g., by a distance D6. FIG. 4B also shows that the lower periphery of the set of struts 114 can include a node which is located above a node of the upper periphery of the set of struts 114. As used herein, above means closer to the upper end of the frame and below means closer to the lower end of the frame.

The frame 102 illustrated in FIGS. 1-4 has fewer struts than known frames, and as a result, the decrease in the number of struts can reduce the overall profile of the prosthetic valve 100 when it is in a crimped state, while retaining structure and strength sufficient to ensure adequate performance of the prosthetic valve. For example, a prosthetic valve 100 including the frame 102 illustrated in FIGS. 1-4 can have a diameter of about 26 mm in its expanded, functional state, and a diameter of about 6.33 mm (about 19 French), or smaller, in its collapsed, crimped state. A similar prosthetic valve having a frame with complete rows of angled struts arrayed along the entire length of the frame from the inflow end to the outflow end typically can be radially compressed from an expanded diameter of about 26 mm to a collapsed diameter of from about 8 mm to about 8.67 mm (from about 24 French to about 26 French).

As noted above, the secondary row 128 is without any struts connecting it to the attachment posts 112A, 112B. Also, the tertiary row 144 is without any struts disposed between the struts 146B and 146C. Thus, the secondary and tertiary rows are partial rows of struts extending partially between the attachment posts 112A, 112B. As can be seen in FIG. 4A, the secondary row 128 is without any struts within the angular segments containing the struts of the tertiary row 144. Likewise, the tertiary row 144 is without any struts within the angular segment containing the struts of the secondary row 128. In this manner, the struts between the attachment posts 112A, 112B have an overall scalloped shape.

Stated differently, the main row 118 and the secondary row 128 define a lower perimeter of the struts 114 having an overall concave shape facing in the direction of the outflow end 110, and the main row 118 and the tertiary row 144 define an upper perimeter of the struts 114 having an overall concave shape facing in the direction of the outflow end 110. Thus, the set of struts 114 comprises no more than two rows of angled struts along any axis aligned with the central longitudinal axis 116 (which can be aligned with the attachment posts and vertical struts 126). In determining the number of rows of struts that exist along an axis aligned with the central longitudinal axis, vertical struts such as the vertical struts 126 are not counted. In other words, no line that is parallel to the central axis 116 intersects more than two angled struts.

In certain embodiments, a larger or smaller number of rows of individual struts 200 can be provided. In other embodiments, a larger or smaller number of struts can be provided in each of the rows of struts. In general, providing additional struts can increase the overall profile of the prosthetic valve 100 in its crimped state, but can increase the strength of the prosthetic valve 100 when in its expanded, functional state. Similarly, reducing the number of struts in the frame 102 can decrease the overall profile of the prosthetic valve 100 in its crimped state, but can also decrease the strength of the prosthetic valve 100 in its expanded, functional state.

Figure 5:
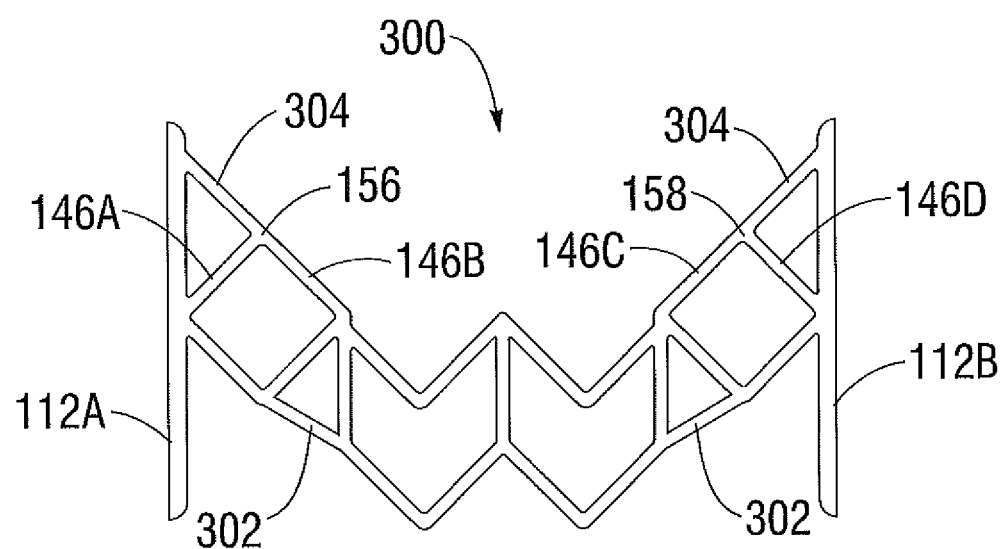
FIG. 5 is a flattened view of a 120-degree segment of an alternative embodiment of a frame that can be used in the prosthetic valve of FIGS. 1-2.

FIG. 5 illustrates a flattened view of another embodiment of a segment of a frame comprising a set of struts 300 having a configuration similar to that of set of struts 114, but with four additional struts. In particular, additional struts 302 can be provided which couple the ends 136, 138 (FIG. 4A) of the secondary row of struts to the bottom apices 124 of the main row 118. Further, two additional struts 304 can be provided. One additional strut 304 can be connected to and extend from the top apex 158 between the struts 146C and 146D to attachment post 112B. The other additional strut 304 can be connected to and extend from the top apex 156 between the struts 146A and 146B to attachment post 112A. The additional struts 302, 304 can increase the strength of a prosthetic valve 100 in its expanded, functional state.

Figure 7:
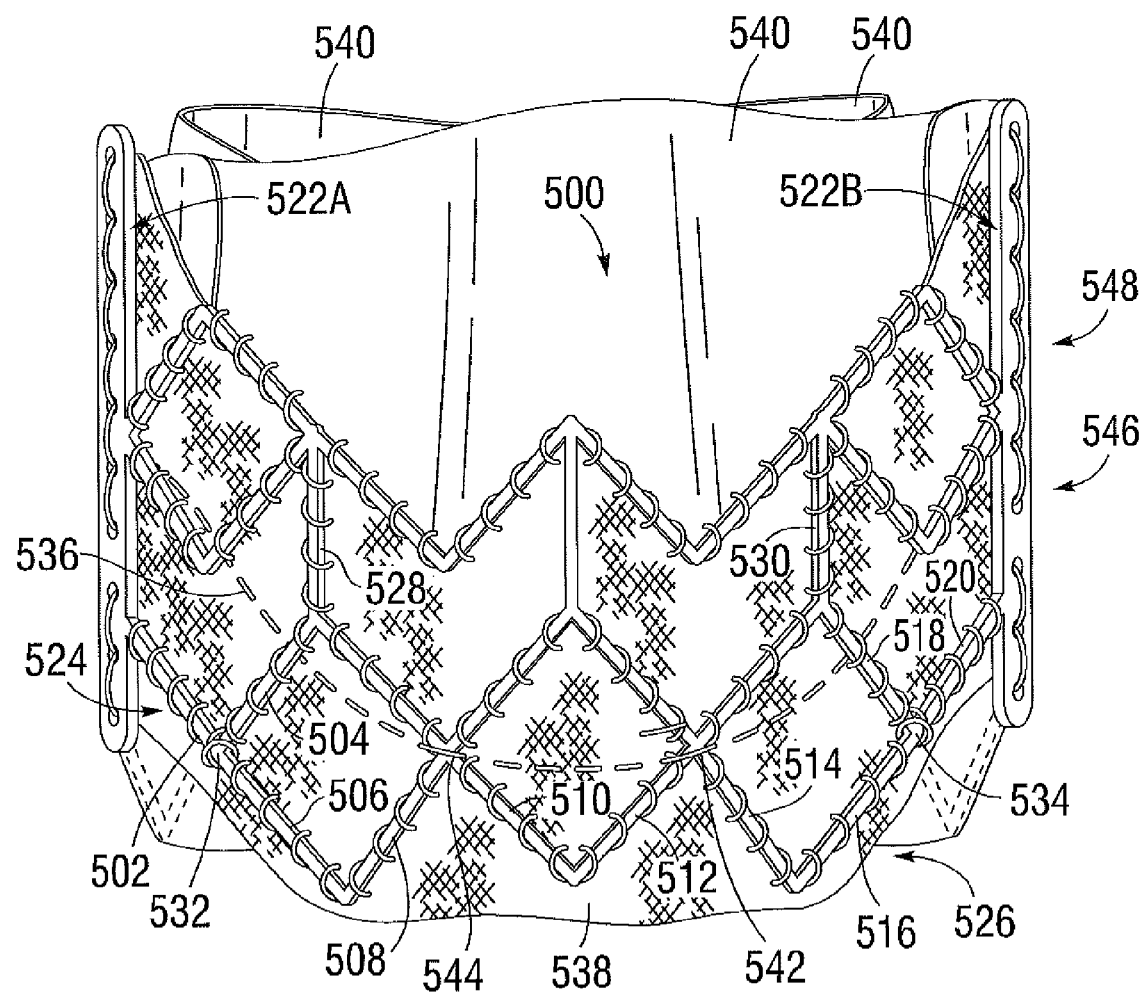
FIG. 7 is a side view of a prosthetic valve including another alternative embodiment of a frame.

FIG. 7 illustrates a prosthetic valve including another embodiment of a set of struts 500. Set of struts 500 has a configuration similar to that of set of struts 114, but with ten additional struts. In particular, the set of struts 500 includes a primary row of struts 546 which extends from attachment post 522A to attachment post 522B, a secondary row of struts 524 which extends from attachment post 522A to attachment post 522B, a tertiary row of struts 548, and a quaternary row of struts 526. Rows of struts 546 and 524 are complete rows of angled struts. Rows of struts 548 and 526 are partial rows of struts.

Thus, set of struts 500 can include additional struts 502 and 504 in the secondary row of struts 524, which can extend in a generally zig-zag or saw-tooth configuration from the bottom of a first vertical strut 528 to the attachment post 522A, thereby forming a secondary bottom apex 532. Set of struts 500 can also include additional struts 518 and 520 in the secondary row of struts 524, which can extend in a generally zig-zag or saw-tooth configuration from the bottom of a second vertical strut 530 to the attachment post 522B, thereby forming a secondary bottom apex 534. Quaternary row of struts 526 can include struts 506, 508, 510, 512, 514, and 516, which can extend in a generally zig-zag or saw-tooth configuration from secondary bottom apex 532 to secondary bottom apex 534. As shown in FIG. 7, a set of struts 500 can include not more than 29 struts, 23 nodes, and 9 cells.

FIG. 7 also illustrates that curved stitching 536 can be used to stitch the skirt 538 to valve leaflets 540. Further, stitching 536 can be used to stitch a skirt 538 and leaflets 540 directly to the frame, such as by stitching over the frame at nodes 542 and 544. Set of struts 500 can be used in place of any set of struts, and/or in combination with any prosthetic valve or components thereof, as described herein or known in the art. The additional struts of set of struts 500 (i.e., those not present in set of struts 114) can increase the strength and/or stability of a prosthetic valve in its expanded, functional state, as compared to the strength and/or stability of known strut configurations.

Figure 8:
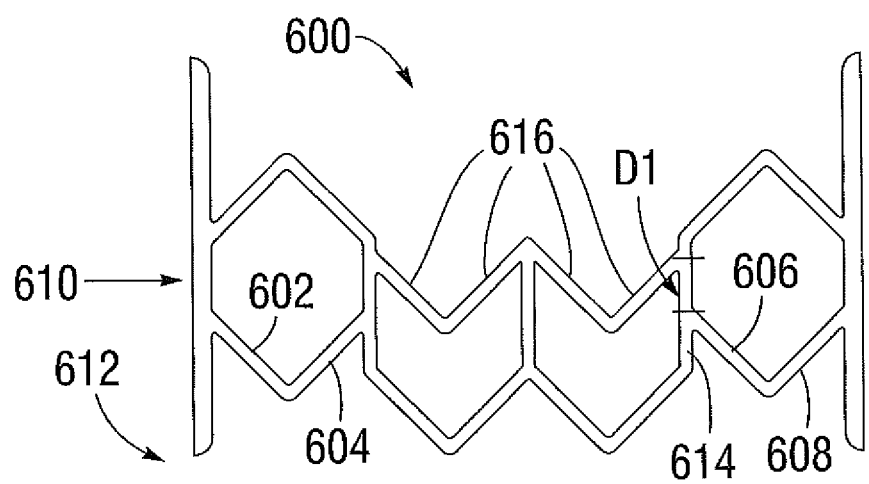
FIG. 8 is a flattened view of a 120-degree segment of an alternative embodiment of a frame that can be used in prosthetic valves.

FIG. 8 illustrates a flattened view of a frame segment comprising another embodiment of a set of struts 600 having a configuration similar to that of set of struts 114 of frame 102. In set of struts 600, struts 602, 604, 606, and 608, are each offset from struts 616 of the main row 610 by a distance D1, toward a lower end 612 of the frame segment. Thus, the main row 610 is a partial row of struts and the struts 602, 604, 606, 608 form a separate offset partial row of struts. In some cases, distance D1 can be about half a length of the strut 614, to which strut 606 is coupled. The frame segment shown in FIG. 8 includes no complete rows of angled struts. As shown in FIG. 8, a set of struts 600 can include not more than 19 struts, 20 nodes, and 4 cells.

Figure 9:
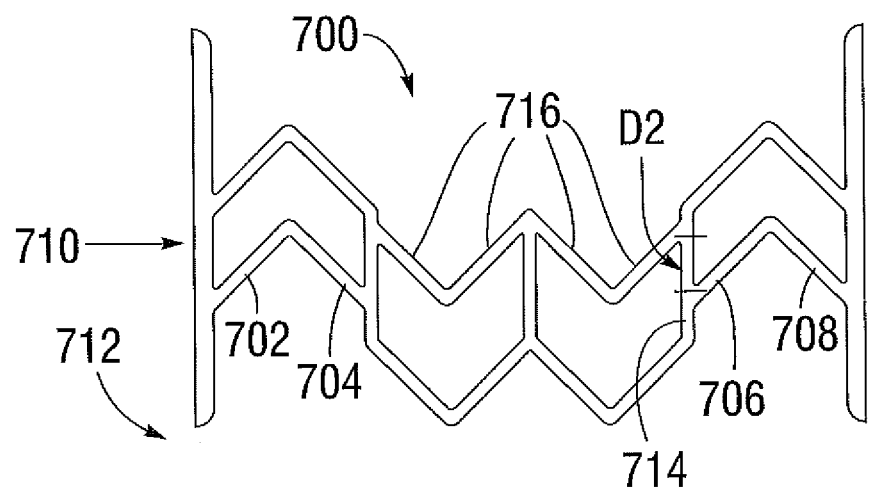
FIG. 9 is a flattened view of a 120-degree segment of another alternative embodiment of a frame that can be used in prosthetic valves.

FIG. 9 illustrates a flattened view of a frame segment comprising another embodiment of a set of struts 700 having a configuration similar to that of set of struts 600. In set of struts 700, struts 702, 704, 706, and 708, are each offset from struts 716 of the main row 710 by a distance D2, toward a lower end 712 of the frame segment. Thus, the main row 710 is a partial row of struts and the struts 702, 704, 706, 708 form a separate offset partial row of struts. In some cases, distance D2 can be half a length of the strut 714, to which strut 706 is coupled. Further, struts 702 and 704 can form a zig-zag or generally saw-tooth arrangement which is inverted relative to the zig-zag arrangement of struts 716 in the main row 710. Similarly, struts 706 and 708 can form a zig-zag or generally saw-tooth arrangement which is inverted relative to the zig-zag arrangement of struts 716 in the main row 710. The frame segment shown in FIG. 9 includes no complete rows of angled struts. As shown in FIG. 9, a set of struts 700 can include not more than 19 struts, 20 nodes, and 4 cells.

Sets of struts 600, 700 can be used in place of any set of struts, and/or in combination with any prosthetic valve or components thereof, as described herein or known in the art. Sets of struts 600, 700 can provide increased strength and/or stability to a prosthetic valve in its expanded, functional state, as compared to the strength and/or stability of known strut configurations.

In alternative embodiments, a pair of adjacent or connected struts can be connected to each other by a respective, generally U-shaped crown structure, or crown portion. Crown structures can each include a horizontal portion extending between and connecting the adjacent ends of the struts such that a gap is defined between the adjacent ends and the crown structure connects the adjacent ends at a location offset from the strut's natural point of intersection. Crown structures can significantly reduce strains on the frame 102 during crimping and expanding of the frame 102. Further details regarding crown structures are available in U.S. Pat. No. 7,993,394, which is incorporated by reference.

In certain embodiments, various struts can have differing cross sections. For example, any of the struts can have a generally circular, triangular, quadrilateral, or other appropriately shaped cross section. Further, the various individual struts 200 can have differing thicknesses or diameters. In one exemplary embodiment, some of the individual struts 200 can have a thickness of about 0.42 mm and some of the individual struts 200 can have a thickness of about 0.38 mm. A larger thickness of the individual struts 200 can enhance the radial strength of the frame 102 and/or allow for more uniform expansion of the frame. Additionally, the cross-sectional area and/or the cross-sectional shape of a particular strut can be variable along its length.

Figure 6:
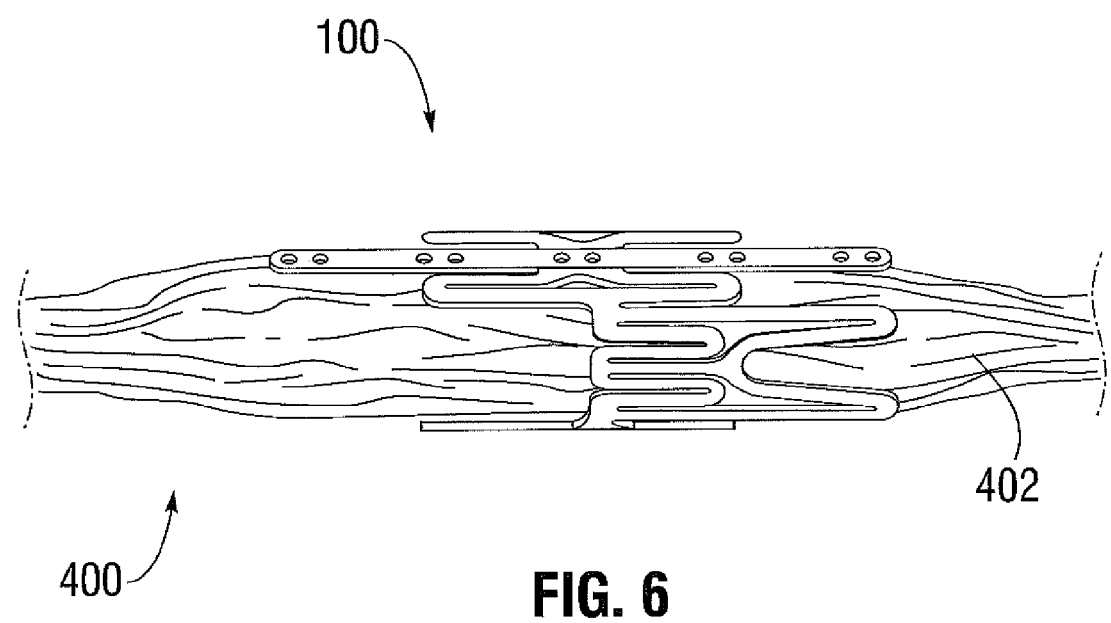
FIG. 6 is a side view of a prosthetic valve crimped onto the balloon of a balloon catheter.

FIG. 6 depicts a side view of a prosthetic valve 100 crimped on a balloon 402 of a balloon delivery catheter 400. It is desirable to protect the leaflet structure 104 of the prosthetic valve 100 from damage during crimping to ensure durability of the leaflet structure 104 and at the same time, it is desirable to reduce as much as possible the crimped profile size of the prosthetic valve 100. If the tissue of the leaflet structure 104 (e.g., bovine pericardial tissue or other suitable tissue) is pressed against the inner surface of the metal frame 102 during crimping, portions of the tissue can protrude into the open cells of the frame between the individual struts 200 and can be pinched due to the scissor-like motion of the individual struts 200 of the frame 102. If the prosthetic valve 100 is severely crimped to achieve a small crimping size, this scissor-like motion can result in cuts and rupture of the tissue leaflets.

The skirt 106, described above, can protect against damage to the leaflet structure 104 during crimping by providing a barrier between the leaflets 152 and the open cells 204 of the frame 102. In addition, since the unique frame design eliminates the struts along a length of the prosthetic valve 100 adjacent the outflow end 110, a significant portion of the leaflets 152 do not come in contact with the individual struts 200 of the frame 102 during crimping, which can further protect against damage to the leaflets 152.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An implantable prosthetic valve comprising:
    an inflow end;
    an outflow end;
    a central longitudinal axis extending from the inflow end to the outflow end;
    a radially collapsible and expandable annular frame comprising a plurality of commissure attachment posts and a plurality of sets of struts,
        wherein the plurality of commissure attachment posts are angularly spaced apart from each other around the central longitudinal axis;
        wherein each set of struts extends circumferentially partially around the central longitudinal axis from a first respective commissure attachment post to a second respective commissure attachment post and comprises a plurality of rows of angled struts arranged in a zig-zag pattern in each row of angled struts, wherein each set of struts comprises at least one complete row of angled struts extending from the first respective commissure attachment post to the second respective commissure attachment post and at least two partial rows of angled struts extending between the first and second respective commissure attachment posts; and a valve member supported within an interior of the radially collapsible and expandable annular frame.

2. The implantable prosthetic valve of claim 1, wherein each set of struts comprises exactly one complete row of angled struts extending circumferentially around the central longitudinal axis from the first respective commissure attachment post to the second respective commissure attachment post.

3. The implantable prosthetic valve of claim 2, wherein each set of struts comprises exactly two partial rows of angled struts extending between the first and second respective commissure attachment posts.

4. The implantable prosthetic valve of claim 3, wherein the two partial rows of angled struts are positioned on opposite sides of the complete row of angled struts.

5. The implantable prosthetic valve of claim 1, wherein each set of struts further comprises a plurality of vertical struts extending between and connecting a first partial row of angled struts to the at least one complete row of angled struts.

6. The implantable prosthetic valve of claim 5, further comprising at least one additional strut extending between and connecting an end of the first partial row of angled struts and an apex of the at least one complete row of angled struts.

7. The implantable prosthetic valve of claim 5, wherein a second partial row of angled struts is coupled to apices of the at least one complete row of angled struts.

8. The implantable prosthetic valve of claim 7, further comprising at least one additional strut extending between and connecting an apex of the second partial row of angled struts and a commissure attachment post.

9. The implantable prosthetic valve of claim 1, wherein each set of struts comprises an upper perimeter and a lower perimeter, each of the upper and lower perimeters having an overall concave shape facing in a direction of the outflow end of the implantable prosthetic valve.

10. The implantable prosthetic valve of claim 1, wherein the radially collapsible and expandable annular frame is self-expandable from a radially collapsed state.

11. The implantable prosthetic valve of claim 10, wherein the radially collapsible and expandable annular frame has an outer diameter of about 19 French in the radially collapsed state.

12. The implantable prosthetic valve of claim 1, further comprising a skirt secured to the radially collapsible and expandable annular frame.

13. The implantable prosthetic valve of claim 12, wherein the skirt is secured to the radially collapsible and expandable annular frame with sutures securing the skirt to the plurality of sets of struts.

14. The implantable prosthetic valve of claim 12, wherein the skirt is secured to the radially collapsible and expandable annular frame with sutures securing the skirt to the radially collapsible and expandable annular frame through openings in the commissure attachment posts.

15. The implantable prosthetic valve of claim 1, wherein each set of struts comprises no more than 19 struts, 16 nodes, and 4 open cells.

16. The implantable prosthetic valve of claim 1, comprising exactly three commissure attachment posts and exactly three sets of struts.

17. An implantable prosthetic valve comprising:
an inflow end;
an outflow end;
a central longitudinal axis extending in an axial direction from the inflow end to the outflow end;
a radially collapsible and expandable annular frame comprising a plurality of commissure attachment posts and a plurality of sets of struts,
wherein the plurality of commissure attachment posts are angularly spaced apart from each other around, and are aligned with, the central longitudinal axis;
wherein each set of struts extends circumferentially partially around the central longitudinal axis from a first respective commissure attachment post to a second respective commissure attachment post;
wherein each set of struts comprises no more than two rows of struts along any axis aligned with the central longitudinal axis;
wherein each set of struts comprises exactly one complete row of angled struts extending circumferentially around the central longitudinal axis from the first respective commissure attachment post to the second respective commissure attachment post; and
a valve member supported within an interior of the radially collapsible and expandable annular frame.

18. The implantable prosthetic valve of claim 17, wherein each set of struts comprises exactly two partial rows of angled struts extending between the first and second respective commissure attachment posts.

19. The implantable prosthetic valve of claim 18, wherein the two partial rows of angled struts are positioned axially on opposite sides of the complete row of angled struts.

* * * * *